US012691085B2

(12) United States Patent
Myntti

(10) Patent No.: US 12,691,085 B2
(45) Date of Patent: Jul. 28, 2026

(54) CANCER TREATMENT COMPOSITION AND METHOD

(71) Applicant: Next Science IP Holdings Pty Ltd, Chatswood (AU)

(72) Inventor: Matthew Myntti, St. Augustine, FL (US)

(73) Assignee: OSARTIS GmbH, Muenster (DE)

( * ) Notice: Subject to any disclaimer, the term of this patent is extended or adjusted under 35 U.S.C. 154(b) by 416 days.

(21) Appl. No.: 18/270,005

(22) PCT Filed: Dec. 28, 2021

(86) PCT No.: PCT/US2021/065412

§ 371 (c)(1),
(2) Date: Jun. 28, 2023

(87) PCT Pub. No.: WO2022/147055

PCT Pub. Date: Jul. 7, 2022

(65) Prior Publication Data

US 2024/0091181 A1 Mar. 21, 2024

Related U.S. Application Data

(60) Provisional application No. 63/131,726, filed on Dec. 29, 2020.

(51) Int. Cl.
*A61K 31/194* (2006.01)
*A61K 33/00* (2006.01)
*A61K 45/06* (2006.01)

(52) U.S. Cl.
CPC ............ *A61K 31/194* (2013.01); *A61K 33/00* (2013.01); *A61K 45/06* (2013.01)

(58) Field of Classification Search
CPC ....... A61K 31/194; A61K 33/00; A61K 45/06
See application file for complete search history.

(56) References Cited

U.S. PATENT DOCUMENTS 9,427,417 B2 8/2016 Myntti
10,477,860 B2 * 11/2019 Myntti .................. A61K 8/416
2016/0038604 A1 * 2/2016 Holbein ................ A01N 43/40
514/59
2020/0163938 A1 5/2020 Nishida et al.

FOREIGN PATENT DOCUMENTS

WO 2022147055 A1 7/2022

OTHER PUBLICATIONS

Frawley et al. The Ins and Outs of Bacterial Iron Metabolism, Mol Microbiol, Aug. 2014, pp. 1-13. (Year: 2014).*

Bates, George, W., et al., "The Kinetics and Mechanism of Iron (III) Exchange between Chelates and Transferrin", The Journal of Biological Chemistry, vol. 242, No. 12, Issue of Jun. 25, 1967, pp. 2810-2815.

Brinckerhoff, C.E., et al., "Matrix metalloproteinases: a tail of a frog that became a prince", Nature Reviews, Molecular Cell Biology, vol. 3, Mar. 2002, pp. 207-214.

Byrne, Shaina L., et al., "The Unique Kinetics of Iron Release from Transferrin: The Role of Receptor, Lobe-Lobe Interactions and Salt at Endosomal pH", J. Mol. Biol. Feb. 12, 2010; 396(1): 130. doi: 10.1016/j.jmb, Nov. 23, 2009, pp. 1-19.

Cathcart, J., et al., "Targeting matrix metalloproteinases in cancer: Bringing new life to old ideas", ScienceDirect, Genes & Diseases, 2015, vol. 2, pp. 26-34.

Clinical Study Report, "Clinical Assessment of the Effects of Next Science Wound Gel on Diagnostic Biopsy Wound Sites of Suspected Non-Melanoma Skin Cancer Lesions", Protocol No. CSP-011, Next Science, Sep. 20, 2021, pp. 1-24.

De Saint Jean, Magdalena, et al., "Effects of Benzalkonium Chloride on Growth and Survival of Chang Conjunctival Cells", Investigative Ophthalmology & Visual Science, Mar. 1999, vol. 40, No. 3, pp. 619-630.

Decaneto, Elena, et al., "Solvent water interactions within the active site of the membrane type I matrix metalloproteinase", Phys. Chem. Chem. Phys., 2017, vol. 19, pp. 30316-30331.

El Hage Chahine, Jean-Michel, et al., "The mechanism of iron release from transferrin: Slow-proton-transfer-induced loss of nitrilotriacetatoiron(III) complex in acidic media", Eur. J. Biochem., 223, pp. 581-587 (1994).

Enomoto, R., et al., "Cationic Surfactants Induce Apoptosis in Normal and Cancer Cells", ANNALS New York Academy of Sciences, 2007, pp. 1-6.

Gaur, K., et al., "Iron and Copper Intracellular Chelation as an Anticancer Drug Strategy", Inorganics, Nov. 6, 2018, 126, pp. 1-38.

Gialeli, Chrisostomi, et al., "Roles of matrix metalloproteinases in cancer progression and their pharmacological targeting", the FEBS Journal 278 (2011), pp. 16-27.

Gomis-Ruth, F. Xavier, "Catalytic Domain Architecture of Metzincin Metalloproteases", The Journal of Biological Chemistry, Jun. 5, 2009, vol. 284, No. 23, pp. 15353-15357.

Lee, David A., et al., "The pH-Induced Release of Iron from Transferrin Investigated with a Continuum Electrostatic Model", Biophysical Journal, vol. 74, Jun. 1998, pp. 2747-2759.

(Continued)

*Primary Examiner* — Sarah Pihonak
*Assistant Examiner* — Mikhail O'Donnel Robinson
(74) *Attorney, Agent, or Firm* — David G. Burleson

(57) ABSTRACT

A method for selectively or preferentially reducing the amount of Fe ions available to cancer cells involves introducing to an area of the body which contains cancer cells an effective amount of an aqueous, pH buffered composition that includes dissociation products of a soluble weak acid and a salt of a weak acid. When the amount of arriving Fe ions falls below a first threshold, the cancer cell no longer can proliferate. When the amount of arriving Fe ions falls below a second threshold, the cancer cell dies.

20 Claims, No Drawings

(56) References Cited

OTHER PUBLICATIONS

Lui, Goldie Y.L., et al., "Targeting cancer by binding iron: Dissecting cellular signaling pathways", Oncotarget, vol. 6, No. 22, Jun. 23, 2015, 18748-18779.
Muri, E.M.F., et al., "Hydroxamic Acids as Pharmacological Agents", Current Medicinal Chemistry, 2002, 9, pp. 1631-1653 (with cover page).
Next Science—2019 Annual Report, Sydney, Australia, Thursday, Apr. 9, 2020, Next Science, 77 total pages.
Next Science Clinical Study Protocol 011, "Clinical Assessment of the Effects of Next Science Wound Gel on Diagnostic Biopsy Wound Sites of Suspected Non-Melanoma Skin Cancer Lesions", Next Science Ltd., Jan. 22, 2020, pp. 1-37.
Next Science Limited 2019 Annual General Meeting, Wednesday, Sep. 25, 2019, Next Science, 7 pages.
Next Science Limited 2020 Annual General Meeting, Wednesday, May 6, 2020, Next Science, 6 pages.
Next Science Limited AGM Presentation, Innovations powered by XBIO technology, Next Science, May 6, 2020, 16 pages.
Next Science Limited Annual General Meeting—presentation, Innovations powered by XBIO technology, Next Science 2019 AGM Presentation, Sep. 25, 2019, 26 pages.
Next Science/JCCR Master Collaboration Agreement, Master Agreement for Specimen Acquisition Collaboration, May 28, 2014, 12 pages.
Ren, Jian-Guo, et al., "Citrate Suppresses Tumor Growth in Multiple Models through Inhibition of Glycolysis, the Tricarboxylic Acid Cycle and the IGF-1R Pathway", Scientific Reports, Jul. 3, 2017, pp. 1-13.
Reunanen, N., et al., "Matrix Metalloproteinases in Cancer Cell Invasion", Madame Curie Bioscience Database—NCBI Bookshelf, 2018, pp. 1-21.
Rundhaug, Joyce E., "Matrix Metalloproteinases, Angiogenesis, and Cancer", Clinical Cancer Research, vol. 9, Feb. 2003, pp. 551-554.
Sans-Fons, M. Gloria, et al., "Matrix Metalloproteinase-9 and Cell Division in Neuroblastoma Cells and Bone Marrow Macrophages", Growth Factors, Cytokines, Cell Cycle Molecules, The American Journal of Pathology, vol. 177, No. 6, Dec. 2010, pp. 2870-2885.
Spiro, Thomas G., et al., "The Hydrolytic Polymerization of Ferric Citrate. I. The Chemistry of the Polymer", Journal of the American Chemical Society, 89, 22, Oct. 25, 1967, pp. 5555-5559.
Spiro, Thomas G., et al., "The Hydrolytic Polymerization of Ferric Citrate. II. The Influence of Excess Citrate", Journal of the American Chemical Society, 89:22, Oct. 25, 1967, pp. 5559-5562.
Tallant, C., et. al., "Matrix metalloproteinases: Fold and function of their catalytic domains", Biochimica et Biophysica Acta, 1803, 2010, pp. 20-28.
Wang, J., et al., "Regulation of cellular iron metabolism", Biochem. J., 2011, vol. 434, pp. 365-381.
Yip, Kenneth W., et al., "Benzethonium Chloride: A Novel Anticancer Agent Identified by Using a Cell-Based Small-Molecule Screen", Cancer Therapy: Preclinical, Clin Cancer Res 2006; 12(18), Sep. 15, 2006, pp. 5557-5569 (with cover page).
Yu, Qin, et al., "Cell surface-localized matrix metalloproteinase-9 proteolytically activates TGF-b and promotes tumor invasion and angiogenesis", Genes & Development, 14, 2000, pp. 163-176 (with cover page).
EPO extended search report in EP appl. No. 21916377.1, mailed Nov. 6, 2024.
A. Levina et al., "Transferrin Cycle and Clinical Roles of Citrate and Ascorbate in Improved Metabolism," ACS Chem. Biol., vol. 14, pp. 893-900, Apr. 11, 2019 (American Chemical Society; Washington, DC).
J.L. Heath et al., "Iron Deprivation in Cancer—Potential Therapeutic Implications," Nutrients, vol. 5, pp. 2836-2859, Jul. 24, 2013 (MDPI; Basel, Switzerland).

* cited by examiner

CANCER TREATMENT COMPOSITION AND METHOD

CROSS REFERENCE TO RELATED APPLICATIONS

This is a national stage entry of international application PCT/US2021/065412, filed on Dec. 28, 2021, which claims the benefit of U.S. patent application Ser. No. 63/131,726 filed on Dec. 29, 2020, the entirety of which is incorporated herein by reference.

BACKGROUND INFORMATION

Tens of million new cancer cases are diagnosed annually, and millions die from cancer each year.

Cancer can affect any organ or type of cell, and each cancer has its own diagnostic approach and treatment considerations. In any given case, the selected approach and specific treatment depends on the type of cancer, the organ (s) affected, staging of the cancer, and con-comitant illnesses or risk factors. Physicians are faced with the choice of treating cancer with a single therapy or a combination of modalities, and the calculus is complicated by every therapy option being limited by factors such as efficacy, side effects, and tolerability.

Clinical and preclinical research continues to be driven by the quest for safe, tolerable and effective cancer treatment options. Some of these include surgeries such as traditional incisions/excisions, cryosurgery, lasers, and hypothermia, all of which are aimed at physically removing as much of the tumor burden as possible; radiation therapy; chemotherapy; hormonal therapy; immunotherapies; and stem cell therapy. Other options include modification of gene expression (epigenetics), where the DNA profile of a patient's specific cancer cells is the focus of attack, and so-called targeted therapies (e.g., monoclonal antibodies and small molecule drugs that are of a size that permit them to enter cancer cells and reach intracellular targets) where specific attributes of the cancer cells are targeted to slow or stop their growth, division and spread.

One option that continues to be of interest is chelation therapy, where chelating agents are used to bind and eliminate substances necessary for cancer cell metabolism and proliferation. One substance of particular interest is iron (Fe); see, e.g., K. Gaur et al., "Iron and Copper Intracellular Chelation as an Anticancer Drug Strategy," *Inorganics,* 2018, 6/126 (Multi-disciplinary Digital Publishing Institute; Basel, Switzerland) and G. Y. L. Lui et al., "Targeting cancer by binding iron: Dissecting cellular signaling pathways," *Oncotarget*, vol. 6, no. 22, pp. 18748-79 (2015) (Impact Journals, LLC; Orchard Park, New York).

All cells require Fe, with many critical physiological functions including oxygen uptake/delivery, ATP synthesis, metabolism and DNA synthesis depending on it. Within the cell, Fe is needed for regulation of a variety of Fe-containing enzymes, including those involved in DNA replication and repair, energy generation in mitochondria, and control of gene expression.

Due to their high rates of DNA synthesis and cell growth, cancer cells have iron requirements far exceeding those of non-cancerous cells. Cancer cells both store less iron as ferritin to be transported out of the cell and use more to support cell genetic activity and proliferation. Because of the reduced iron storage in cancer cells, they quickly run out of iron and die if iron in the extracellular environment becomes unavailable due to having been chelated. Iron chelators that deplete cellular iron level have been shown to suppress the growth of certain cancers.

A variety of iron-targeted compounds are being studied as targeted therapies. These include siderophores (molecules that bind and transport iron) such as Deferoxamine (DFO), Deferasirox and Deferiprone; thiosemicarbazones, which both bind iron in the cell and inhibit the ribonucleotide reductase (RR) enzyme to limit the amount of iron entering the cell; and hydrazones, which have a mode of action similar to DFO. Other molecules under study for iron depletion of cancer cells target the synthesis of the ferritin iron storage protein and induction of oxidative stress, leading to cell death.

Despite continued interest and investigation, chelation therapy suffers from several inherent drawbacks. It tends to indiscriminately decrease the availability of Fe to all types of cells. Also, Fe-containing nutrients present a renewed source of Fe which, in turn, requires further chelation. Additionally, unless the chelating agent is very specific for Fe, which is unusual, it will complex with one or more other transition metals as well, thereby making them unavailable for intracellular activities. Finally, as described in more detail below, ferric ions at physiological pH form an exceedingly stable complex with transferrin, the dissociation constant of which is so high that even exceptional chelating agents have difficulty competing.

Nevertheless, the importance of Fe to cancer cell survival and proliferation means that methods for preferentially reducing Fe available to cancer cells so as to reduce the amount available for metabolic processes below the level necessary for survival continue to be of significant interest. Of particularly interest would be a Fe-reducing method which impacted non-cancer cells less than cancer cells.

SUMMARY

Hereinafter is described a method for selectively or preferentially reducing the amount of Fe ions available for entry to and use by targeted abnormal dermal cells. The method involves applying to a dermal area in need thereof an effective amount of a composition that includes an aqueous, pH buffered liquid that includes dissociation products of a soluble weak acid and a conjugate base of a weak acid in a vehicle that permits the composition to be provided in semi-solid form. The pH of the liquid is below 6.5, often below 6, and typically below 5.5.

Also provided is an aqueous composition having a solute component that includes sufficient amounts of anions from a weak acid plus both hydronium and metal cations so as to provide a buffered pH below 6.5. The composition is provided for application to a dermal area that includes cancer cells or precursors thereof, e.g., a precancerous lesion. The composition advantageously inhibits or even prevents $Fe^{+3}$ ions from entering nearby cells, thereby leading to the weakening and/or death of those cells which have reduced amounts of stored $Fe^{+2}$ ions available for use.

The composition advantageously is generally considered biocompatible. External exposure results in no long-term negative dermal effects whereas internal exposure can result in biodegradation and/or biosorption.

The composition advantageously is non-toxic or, at worst, has very low toxicity. The ingredients are generally considered to be biocompatible.

Other aspects of the invention will be apparent to the ordinarily skilled artisan from the detailed description that follows. To assist in understanding that description, certain definitions are provided immediately below, and these are intended to apply throughout unless the surrounding text explicitly indicates a contrary intention:

"comprising" means to include, but not be limited to, the listed ingredients or steps;

"consisting of" means to include only the listed ingredients (or steps) and minor amounts of inactive additives or adjuvants;

"consisting essentially of" means to include only the listed ingredients (or steps), minor amounts (less than 5%, 4%, 3%, 2%, 1%, 0.5%, 0.25%, or 0.1%) of other ingredients that supplement activity and/or provide a secondary effect desirable in view of the intended end use, and/or inactive additives or adjuvants;

"polyacid" means a compound having at least two carboxyl groups and specifically includes dicarboxylic acids, tricarboxylic acids, etc.;

"pH" means the negative value of the base 10 logarithm of $[H^+]$ as determined by an acceptably reliable measurement method such as a properly calibrated pH meter, titration curve against a known standard, or the like at room temperature (e.g., 20° to 25° C.);

"$pK_a$" means the negative value of the base 10 logarithm of a particular compound's acid dissociation constant;

"buffer" means a compound or mixture of compounds having an ability to maintain the pH of a solution to which it is added within relatively narrow limits;

"buffer precursor" means a compound that, when added to a mixture containing an acid, results in a buffer;

"benzalkonium chloride" refers to any compound defined by the following general formula (I)

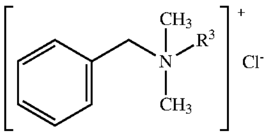

where $R^3$ is a $C_8$-$C_{18}$ alkyl group, or any mixture of such compounds;

"effective solute concentration" is a measurement, presented in units of osmoles per liter, of the colligative property resulting from the number of moles of molecules (from nonelectrolyte) or ions (from electrolytes) present in a given solution;

"$\delta_p$" is the dipolar intermolecular force Hansen Solubility Parameter (HSP), with the value for a solution or mixture of solvents being calculated by general formula (II), $$\delta_p = \sum_{i=1}^{n} (\delta_{di} \times x_{di}) \quad \text{(II)}$$

where $\delta_{di}$ is the energy from dipolar intermolecular force for solvent component i, $X_{di}$ is the percentage of solvent component i relative to the total amount of solvent components, and n is the total number of solvent components;

"substituted" means containing a heteroatom or functionality (e.g., hydrocarbyl group) that does not interfere with the intended purpose of the group in question;

"biocompatible" means presenting no significant, long-term deleterious effects on or in a mammalian species;

"biodegradation" means transformation, via enzymatic, chemical or physical in vivo processes, of a chemical into smaller chemical species;

"biosorption" means absorption of a material into the body of a mammalian species;

"cancer" means uncontrolled growth, and optionally spread, of abnormal cells in a particular organ, which can take the form of solid tumors, lymphomas, and non-solid cancers such as leukemia;

"malignant" refers to cells that have the capacity to metastasize, with loss of both growth and positional control;

"tumor" refers to abnormal new cell or tissue growth, which may be benign or malignant;

"treat" means to inhibit, delay or prevent onset or progression of cancer including cancer and/or metastasis in a mammal, particularly a human;

"treatment" means a protocol or procedure for treating; and

"active anti-cancer agent" means any of the following compounds, as well as pharmaceutically acceptable salts or hydrates, free acids, free bases, or other free forms of such compounds, which do not interfere with the inventive method: suberoylanilide hydroxamic acid; (1R)-3-methyl-1-[[(2S)-1-oxo-3-phenyl-2-[(pyrazinylcarbonyl)amino]-propyl]amino]butyl] boronic acid (Bortezomib); polar compounds (P. A. Marks et al. (1987) *Cancer Res.* 47: 659; C. Friend et al. (1971) *Proc. Natl. Acad. Sci.* (USA) 68: 378-82; M. Tanaka et al. (1975) *Proc. Natl. Acad. Sci.* (USA) 72: 1003-06; and R. C. Reuben et al. (1976) *Proc. Natl. Acad. Sci.* (USA) 73: 862-66)); derivatives of vitamin D and retinoic acid (E. Abe et al. (1981) *Proc. Natl. Acad. Sci.* (USA) 78: 4990-94; E. L. Schwartz et al. (1983) *Proc. Am. Assoc. Cancer Res.* 24: 18; K. Tanenaga et al. (1980) *Cancer Res.* 40: 914-19)); steroid hormones (J. Lotem et al. (1975) *Int. J. Cancer* 15: 731-40)); growth factors (L. Sachs (1978) *Nature* (*Lond.*) 274: 535; D. Metcalf (1985) *Science,* 229: 16-22); proteases (W. Scher et al.. (1983) *Exp. Hematol.* 11: 490-98; W. Scher et al. (1982) *Biochem. & Biophys. Res. Comm.* 109: 348-54)); tumor promoters (E. Huberman et al. (1979) *Proc. Natl. Acad. Sci.* (USA) 76: 1293-97; J. Lottem et al. (1979) *Proc. Natl. Acad. Sci.* (USA) 76: 5158-62)); and inhibitors of DNA or RNA synthesis (E. L. Schwartz et al. (1982) *Cancer Res.* 42: 2651-55; M. Terada et al. (1978) *Proc. Natl. Acad. Sci.* (USA) 75: 2795-99; M. J. Morin et al. (1984) *Cancer Res.* 44: 2807-12; E. L. Schwartz et al. (1983) *Cancer Res.* 43: 2725-30; H. Sugano et al. (1973) *Bibl. Hematol.* 39: 943-54; P. S. Ebert et al. (1976) *Cancer Res.* 36: 1809-13; M. Hayashi et al. (1979) *Gann* 70: 235-38).

Throughout this document, unless the surrounding text explicitly indicates a contrary intention, all values given in the form of percentages are w/v, i.e., grams of solute per liter of composition.

Recited numerical limitations include an appropriate degree of precision based on the number of significant places used; for example, "up to 5.0" can be read as setting a lower absolute ceiling than "up to 5."

The relevant portion(s) of any specifically referenced patent and/or published patent application are incorporated herein by reference.

DETAILED DESCRIPTION OF ILLUSTRATIVE EMBODIMENTS

The Background section above explains the role of Fe in cells and potential benefits and drawbacks of chelation. The composition and method briefly described in the Summary section are not believed to per se chelate Fe atoms/ions but, instead, to reduce their availability to cancer cells by gentle yet biologically significant manipulation of extracellular pH levels.

A more detailed discussion of the roles of Fe and how it is used follows. For additional details, the interested reader is directed to J. Wang et al., "Regulation of cellular iron metabolism," *Biochem. J.,* 2011, 434, pp. 365-81 (Biochemical Society; London, UK).

Despite the numerous uses for Fe, adult human bodies typically contain less than 4 g, meaning that Fe constitutes roughly 0.005% (w/w) of a 70 kg person. Mammals do not possess any regulated excretion method for excess Fe; instead, they tightly regulate the uptake of Fe during dietary absorption in the duodenum, with the hormone hepcidin playing a key role.

Only ~0.1% (w/w) of the total Fe amount circulates through the body in plasma. The correct levels of Fe in the body and individual cells are closely controlled by complex systems of Fe regulation to keep Fe available at the desired level.

Essentially all Fe in plasma is carried by the transport protein transferrin (TF), a relatively large glycoprotein with homologous N- and C-terminal Fe-binding domains, each being divided into two sub-domains, with a so-called cleft between the sub-domains. Each cleft "closes" when an Fe atom is present and "opens" when the Fe atom is released. The result can be mono- or diferric transferrin, depending on whether one or two cleft-centered complexes are present.

The oxidation status of the Fe atom impacts how it interacts with the TF terminal domain clefts. For example, at typical physiological pH, the terminal domain clefts form extremely stable complexes with $Fe^{+3}$ (dissociation constant on the order of $10^{20}$ $M^{-1}$ or higher), but significantly less stable complexes with $Fe^{+2}$. The stability of the ferric complexes ensures solubility of transported Fe under physiologic conditions (because ferric ions typically would be expected to form essentially insoluble salts at neutral or slightly basic pH), prevents Fe-mediated free radical toxicity, and facilitates transport to, and then into, cells. (This latter feature is discussed in more detail below.)

Each of the aforementioned cleft areas is believed to provide four coordinating atoms, but their ability to complex (bind) ferric iron is negligible without the presence of a so-called bridging ligand between the iron and the protein (believed to be a carbonate or bicarbonate anions), which excludes water molecules from the other two available coordination sites. Once the bridging ligand(s) is/are in place, however, the resulting complex is exceedingly stable at physiologic pH. (See also D. A. Lee et al., "The pH-Induced Release of Iron from Transferring Investigated with a Continuum Electrostatic Model," *Biophysical Journal,* 1998, vol. 74, pp. 2747-59 (Biophysical Society; Rockville, Maryland).)

This stable complex is transported to cells throughout the body via plasma and then traverses the extracellular space or matrix. The pH of this extracellular space is very similar to that of the transporting plasma, i.e., neutral or very slightly basic.

In the highly stable complex form, arriving iron is unavailable to the cells. Further, intracellular processes employ iron in the $Fe^{+2}$ (ferrous), as opposed to the $Fe^{+3}$ (ferric), oxidation state. Both issues are addressed inside the cells themselves.

The iron-transferrin complex binds to a transferrin 1 receptor at the surface of a cell membrane. This receptor has a high affinity for transferrin generally, with the affinity increasing from apotransferrin to the monoferric complex and then, particularly, the diferric complex. Cellular transferrin receptors ordinarily are fully saturated, given a typical overall circulating transferrin concentration (~25 mM).

After a receptor receives a transferrin complex, invagination of a clathrin-coated pit with formation of an endocytic vesicle permits a cell to internalize the received Fe-TF complex.

Due to the activity of ATP-dependent proton pumps present in the membrane of an endosome, the endosomal pH typically is maintained at 5.5±1. This reduction in pH is believed to result in protonation of the carbonate/bicarbonate bridging ligand and a conformational change in the cleft-area proteins of the transferrin, thereby weakening association of a cleft with its $Fe^{+3}$ ion; see the aforementioned D. A. Lee et al. article as well as S. L. Byrne et al., "The Unique Kinetics of Iron Release from Transferrin: The Role of Receptor, Lobe-Lobe Interactions and Salt at Endosomal pH," *J. Mol. Biol.,* 2010, 396(1), pp. 130-40 (Elsevier Ltd.; London, UK).

Notwithstanding the foregoing changes to the $Fe^{+3}$-transferrin complex, the $Fe^{+3}$ ion normally still would not dissociate from TF complex in the several minutes between its endocytosis and the return of the apotransferrin-receptor structure to the cell surface. When the transferrin-bound $Fe^{+3}$ ion encounters the lower pH of the endosome (relative to the higher pH of the extracellular matrix), it dissociates from the TF complex and is reduced to the $Fe^{+2}$ state by a plasma membrane oxidoreductase, further weakening the association of the complex. Combined with conformational changes that occur in the structure of the receptor, a free $Fe^{+2}$ ion becomes available for use within the endosome, and the intact apotransferrin-receptor structure migrates back to the cell membrane surface where the apotransferrin can be released when it encounters the higher pH of the extracellular space and return to circulation for additional cycles.

Each $Fe^{+2}$ ion becomes part of the so-called labile iron pool, available for delivery to various intracellular locations including, for example, mitochondria (for heme biosynthesis), RR (for protein and DNA synthesis) and ferritin (storage).

As more $Fe^{+3}$ ions arrive, non-cancerous ("healthy") cells maintain a rough homeostasis by exporting an essentially equivalent number of ferrous ions via ferroportin-1. (Cells may also accommodate excess intracellular iron by secretion of heme or by detoxification and storage as ferritin.)

The transport of Fe to cancerous cells is the same as the process just described for non-cancerous cells. A major difference lies in what happens when Fe arrives at the cell membrane. Disruption of normal iron homeostasis is one tactic used by cancer cells to gain a survival advantage, allowing for greater internal Fe supply to feed their increased proliferation and growth potential. Cancer cells accomplish this by increasing the entry of $Fe^{+3}$ into the cell, decreasing $Fe^{+2}$ elimination and/or disrupting normal iron storage processes.

The increased tendency of cancer cells to proliferate results in increased usage of nutrients and oxygen which, in turn, calls for more use of intracellular Fe.

In addition to using more Fe ions in their own maintenance, cancer cells also employ Fe ions to affect a tumor's surrounding environment, i.e., to facilitate proliferation. Some evidence suggests that elevated Fe levels protect some types of cancer cells from immune system cell breakdown. Iron also increases and stabilizes some matrix metalloproteinases (MMPs), Ca ion-dependent endopeptidases which require coordination of a Zn ion, that degrade the matrix in the extracellular space and permit formation of additional cancer cells created by and from those which preexisted. MMPs also employ transition metals including, significantly, Fe.

To satisfy their need for more iron, cancer cells increase expression of RR, of oxidoreductase, and of transferrin 1 receptors (which increases the ability of the cancer cells to uptake $Fe^{+3}$ ions) and reduce their expression of ferroportin-1. Cancer cells also store less Fe in ferritin, instead dedicating it for proliferation-enabling purposes.

Without intending to be bound by theory, the components of the aqueous buffered composition are believed to reduce the pH of the area around the cell (e.g., the extracellular matrix) to less than neutral and, perhaps, no more than that which is experienced inside the endosome, i.e., pH ≤5.5. If so, the composition has the effect of interfering with or interrupting the stability of the mono- and/or diferric transferrin complexes before they can reach a cancer cell and, in fact, reducing the ferric ions to ferrous ions. Fewer $Fe^{+3}$-TF complexes in the extra-cellular matrix mean, in turn, that cellular transferrin receptors do not encounter as many arriving $Fe^{+3}$-TF complexes, preventing those receptors from being able to transport $Fe^{+3}$ ions to the endosome for intracellular reduction and usage.

The foregoing is distinct from $Fe^{+3}$ complexation. Although certain organic acids can complex Fe ions (described below), the primary mechanism in the present method does not appear to be due solely and, perhaps, even in part, to complexation.

Instead, by downwardly adjusting the pH of fluid(s) in the extracellular space, the present composition and method have the effect of interfering with or interrupting the stability of the mono- and/or diferric transferrin complexes before they can reach the cell. This might occur through one or more of protonation of the necessary linking anion, a change in the conformation of the cleft area involved in complexing the ferric ion, reduction of the $Fe^{+3}$ ion to the $Fe^{+2}$ state (when a reducing agent is present in the composition), or even some other mechanism.

Regardless of how this stability interruption occurs, iron transport into local cells appears to be significantly impacted.

Further, this interruption appears to impact cancer cells to a far greater extent than non-cancer cells. This might be due to the amount of incoming $Fe^{+3}$ ions being reduced below the minimum required critical level but not so low as to impact non-cancerous cells (which require less than this minimum required critical level to maintain function), to the fact that cancer cells have a smaller amount of ferritin-stored $Fe^{+2}$ ions, or both.

Although not prohibited, the present treatment composition might not require introduction into a cancer cell itself to work. Instead, the composition can be introduced to the vicinity of cancerous cells. Again, by interfering with the natural pH surrounding the cancer cells, the composition greatly reduces the amount of arriving $Fe^{+3}$ ions available for use by the cancer cells.

Assuming the foregoing to be true, the present method permits a variety of ways for introducing a composition to the vicinity of a tumor.

Skin cancers are ubiquitous, being the most common of all human cancers: more than 1,000,000 people are diagnosed annually in the United States alone with some type of skin cancer. Their prevalence increases in warmer climates (where sun exposure is more common) and in fair-skinned populations.

These cancers typically are categorized as melanoma or non-melanoma, with the latter including squamous cell and basal cell types of cancer. (Other, far less common skin cancers also exist.) Squamous cell carcinomas commonly present as well-defined, red, scaly, thickened bumps which often tend to ulcerate and bleed. Basal cell carcinomas, the most common type of skin cancer, can invade the surrounding tissue and grow into nerves and bones, causing damage and disfigurement. Melanomas frequently develop in moles, although they can appear as new dark spots on other areas of the skin.

While melanomas are both aggressive and likely to metastasize, non-melanoma cancers are unlikely to metastasize. (Certain populations, for example diabetic patients with chronic inflammation, are more susceptible to metastasis of even non-melanoma skin cancers.)

Skin cancers tend to start as precancerous lesions, which are non-cancerous changes in skin (dysplasia) that can become cancerous over time. Common dysplasia include actinic keratoses (which tend to develop mostly into squamous cell carcinoma) and abnormal moles.

A patient suffering from a skin cancer or a precancerous lesion can be treated by delivering the composition by means of injection at or near the lesion. The amount to be injected can range from 0.05 to 5 mL, typically 0.25 to 3.5 mL. Multiple injections around the periphery of the tumor, and even into the tumor itself, can be performed, typically over the course of up to 60, more typically from 2 to 45, and most typically from 3 to 30 days.

For tumors or lesions primarily at or near the surface of the skin, possible treatments include topical application(s) of an inventive composition to the lesion and/or the dermal area surrounding it. In this procedure, multiple applications of sufficient composition to exceed the perimeter of the tumor over the course of 14 to 90, preferably 18 to 84, more preferably 21 to 76 days are preferred. To assist in keeping the composition in place over an extended period of time, providing the composition in a gel, cream, paste, salve, etc., vehicle can be preferred.

The amount of composition introduced to or near such non-dermal cancer cells, as well as the dosing schedule, depends primarily on the size of the area to be treated as well as, to a lesser extent, the availability of that area for receiving doses of the composition. For example, a relatively inaccessible area might require surgical insertion of a device or eluting solid which can deliver composition over an extended period of time, whereas a more accessible area might allow for periodic injections.

As long as a particular composition is not extremely toxic to non-cancerous cells in the vicinity of the cancer cells (which typically is the case), keeping the composition in place at a given location for an extended period of time typically is not problematic, particularly relative to the undesirability of leaving in place the cancer cells.

The foregoing discussion regarding interference with Fe transport into treated cells is not to be considered limiting. While consistent with data seen to date, it has yet to be proven definitively. Observed activity might be due in whole or part to other mode(s) of action.

One such mode that is consistent with other experimentation conducted on compositions of the type at issue here relates to impact on MMPs. These endopeptidases work on substrates spanning a vast assortment of extracellular components, and their enzyme substrate preference has been used to classify the family into subgroups, some of which are involved in processes and signaling pathways for angiogenesis, cell migration, cell proliferation, apoptosis, differentiation, and the activation of other MMPs.

Nearly all MMPs share certain structural elements: an N-terminal sequence which dictates the localization of each MMP, a propeptide region, a calcium-dependent active site which coordinates a catalytic zinc ion, a linker region of varying length, and a hemopexin-like domain. Aside from the catalytic zinc ion required for proteolysis, a structural zinc and at least one structural calcium ion can be found within the active site of all MMPs.

Cancerous cells are known to express higher quantities and different ratios of MMPs as part of their effort to create "space" for new cancer cells formation, i.e., tumor growth.

For example, MMPs are present in nearly all human cancers, and can influence the tumor environment by promoting angiogenesis (by degrading basement membranes and allowing endothelial cell invasion, thus influencing the growth potential of primary tumors as well as their metastatic lesions), tumor growth, and metastasis. MMP-11 is produced by stromal cells that surround malignant tumors.

Transcription of MMPs usually is tightly regulated and expression generally is low. However, altered MMP expression is correlated to increased cancer proliferation, tumor aggressiveness, and poor prognosis; the expression of MMPs in cancers by normal tumor-associated cells often is the rule, rather than the exception. Nearly every member of the MMP family has been found to be dysregulated in human cancers, particularly MMP−1, −2, −7, −9, −13, and −14.

Early expression of MMPs, either by tumor cells or by surrounding stromal cells, contributes to ECM remodeling, and the release of membrane-bound growth factors creates a more favorable microenvironment for primary tumor establishment. Further upregulation of MMP expression, in particular the gelatinases, allows tumor cells to invade adjacent stroma, break down the basement membranes associated with capillaries and lymphatic vessels, and enter circulation.

For more information on the nature and activity of MMPs, the interested reader is directed to any of a number of journal articles including, for example, N. Reunanen et al., "Matrix Metalloproteinases in Cancer Cell Invasion," in Madame Curie Bioscience Database at www.ncbi.nlm.nih.gov/books/NBK6598/ (link active as of date of filing), Q. Yu et al., "Cell surface-localized matrix metalloproteinase-9 proteolytically activates TGF-β and promotes tumor invasion and angiogenesis," *Genes & Dev.,* 2000, vol. 14, pp. 163-76 (Cold Spring Harbor Laboratory Press; Cold Spring Harbor, NY), M. G. Sans-Fons et al., "Matrix Metalloproteinase-9 and Cell Division in Neuroblastoma Cells and Bone Marrow Macrophages," *Am. J. Pathology*, vol. 177, no. 6, pp. 2870-85 (December 2010) (American Society for Investigative Pathology; Rockville, Maryland), C. E. Brinckerhoff et al., "Matrix metalloproteinases: a tail of a frog that became a prince," *Nature Reviews\Molecular Cell Biology*, vol. 3, pp. 2017-14 (2002) (Nature Publishing Group; New York, New York), C. Gialeli et al., "Roles of matrix metalloproteinases in cancer progression and their pharmacological targeting," FEBS Journal, 278 (2011), pp. 16-27 (John Wiley & Sons, Inc.; Hoboken, New Jersey), J. E. Rundhaug, "Matrix Metalloproteinases, Angiogenesis, and Cancer," *Clin. Cancer Res*., vol. 9, pp. 551-54 (2003) (Am. Assn. for Cancer Research; Philadelphia, Pennsylvania), and J. Cathcart et al., "Targeting matrix metalloproteinases in cancer: Bringing new life to old ideas," *Genes & Diseases,* 2 (2015), pp. 26-34 (Elsevier B. V.; Amsterdam, Netherlands).

Certain acids/conjugate bases which can be used in the composition are known to complex many types of transition metals. One such transition metal is Zn, which happens to be present in MMPs.

Where a composition contains an acid and/or conjugate base that can act as a complexing agent, e.g., citric acid and citrates, the presence of such a complexing agent might act to inhibit MMP activity related to tumor growth. For more information on the role of metal ions in the activity of MMPs and possible inactivation of those metal ions, the interested reader is directed to any of a number of journal articles including, for example, C. Tallant et al., "Matrix metalloproteinases: Fold and function of their catalytic domains," *Biochimica et Biophysica Acta,* 1803 (2010) pp. 20-28 (Elsevier B. V.; Amsterdam, Netherlands), E. M. F. Muri et al., "Hydroxamic Acids as Pharmacological Agents," *Current Medicinal Chem.,* 2002, vol. 9, pp. 1631-53 (Bentham Science Publishers Ltd.; Oak Park, Illinois), E. Decaneto et al., "Solvent water interactions within the active site of the membrane type I matrix metalloproteinase," *Phys. Chem. Chem. Phys.,* 2017, vol. 19, no. 45, pp. 30316-31 (Royal Soc. of Chemistry; London, UK), and F. X Gomis-Rüth, "Catalytic Domain Architecture of Metzincin Metalloproteases," *J. Biol. Chem*., vol. 284, no. 23, pp. 15353-57 (2009) (Am. Soc. for Biochem. and Molecular Biology, Inc.; Rockville, Maryland).

Also envisioned are utilization of one or more of the present methods with one or more other treatment option including, but not limited to, those set forth in the Background section above and/or a treatment involving one or more active anti-cancer agents.

The composition now is described first in terms of its properties and components, many of which are widely available and relatively inexpensive.

The composition includes solvent and solute components.

The solvent component of the composition typically includes a significant amount of water. Relative to its overall volume, exemplary compositions include at least 20%, 25%, 30%, 33%, 35%, 40%, 45%, 50%, or even 55% (all v/v); on a per liter basis, a composition often includes from 300 to 925 mL, commonly from 350 to 920 mL, typically from 400 to 910 mL, and more typically from 450 to 900 mL water. The water preferably is treated (e.g., distilled and/or deionized) and, where necessary, appropriately sterilized.

In many embodiments, the solvent component consists of, or consists essentially of, water.

Although not expected to be necessary for many embodiments of the method, the solvent component of the composition can include at least one organic liquid. Exemplary liquids and how to combine them with one another and/or water to achieve a targeted $\delta_p$ value can be found in, for example, U.S. Pat. No. 10,021,876, with amounts listed there being downwardly adjusted because of the different intended usage.

Because of the intended dermal or internal contact by the composition, organic liquids are limited to those generally recognized as safe by an appropriate regulatory body (e.g., U.S. Food and Drug Administration), and only at levels which fall within usage guidelines approved by those regulatory bodies. Contemplated preferred organic liquids include glycerin, $C_2$-$C_6$ and $C_{12}$-$C_{20}$ alcohols (particularly ethanol, isopropanol, and cetyl alcohol), $C_{16}$-$C_{20}$ oils, and DMSO, with the latter being contemplated as capable of acting as an excellent vehicle for transporting substances through tissue, including skin.

The organic liquid(s) often is/are present at concentrations of no more than 25%, typically 0.5 to 22.5%, and preferably 1 to 20% (all w/v, based on total volume of solvent component). All of the foregoing are subject to the proviso that the solute component, described below, must be able to be solubilized in the solvent component; thus, if a given solute (e.g., citric acid) has limited solubility in a given organic liquid, the amount of that liquid must be kept sufficiently low to permit the other subcomponents of the solvent component to solubilize it.

The presence of one or more organic liquids can be preferable in those situations where an active anti-cancer agent is desired to be included as a solute component. Many of those agents are sparingly soluble or even insoluble in water, so the presence of one or more organic liquids that assist in solubilizing such agent(s) can be desirable.

The composition is somewhat acidic. Generally, the composition has a pH of no more than 6.5, preferably no more than 6.2, more preferably no more than 6.0, even more preferably no more than 5.8, still more preferably no more than 5.6, yet still more preferably no more than 5.4, and most preferably no more than 5.2. The composition also generally has a pH of no less than 3.0, preferably no less than 3.2, more preferably no less than 3.4, even more preferably no less than 3.6, and still more preferably no less than 3.8. Ranges of pH values employing each of the lower limits in combination with each of the upper limits are envisioned. Exemplary pH values of the composition include 5.0±0.9, 4.9±0.9, 4.8±0.8, and 4.75±0.8.

Acidity can be achieved by adding to the solvent component (or vice versa) one or more weak acids, preferably those having $pK_a$ values greater than ~1, greater than ~1.5, greater than ~2, greater than ~2.5, greater than ~3, greater than ~3.5, greater than ~4, greater than ~4.5, greater than ~5, and even greater than ~5.5. Acids with lower $pK_a$ values, particularly mineral acids such as HCl, $H_2SO_4$, $H_3PO_4$, $HNO_3$, $H_3BO_3$, and the like, typically are used only to adjust a composition down to a target pH.

Exemplary weak acids include organic acids, particularly organic polyacids. Monoprotic organic acids such as formic acid, acetic acid and substituted variants (e.g., hydroxyacetic acid, chloroacetic acid, dichloroacetic acid, phenylacetic acid, and the like), propanoic acid and substituted variants (e.g., lactic acid, pyruvic acid, and the like), any of a variety of benzoic acids (e.g., mandelic acid, chloromandelic acid, salicylic acid, and the like), glucuronic acid, and the like. Diprotic organic acids include oxalic acid and substituted variants (e.g., oxamic acid), butanedioic acid and substituted variants (e.g., malic acid, aspartic acid, tartaric acid, citramalic acid, and the like), pentanedioic acid and substituted variants (e.g., glutamic acid, 2-ketoglutaric acid, and the like), hexanedioic acid and substituted variants (e.g., mucic acid), butenedioic acid (both cis and trans isomers), iminodiacetic acid, phthalic acid, and the like. Triprotic organic acids include citric acid, 2-methylpropane-1,2,3-tricarboxylic acid, benzenetricarboxylic acid, nitrilotriacetic acid, and the like. Tetraprotic organic acids include prehnitic acid, pyromellitic acid, and the like. Penta-, hexa-, heptaprotic, etc., organic acids also can be used.

Where a polyprotic acid is used, one or more of the carboxyl protons can be replaced by cationic moieties (e.g., alkali metal ions), which can be the same or different. For example, mono-, di- and trisodium citrate all constitute potentially useful buffer precursors, whether used in conjunction with citric acid or another organic acid. However, because tri-sodium citrate has three available basic sites, it has a theoretical buffering capacity up to 50% greater than that of disodium citrate (which has two such sites) and up to 200% greater than that of sodium citrate (which has only one such site).

Preference is given to those organic acids which are, or can be made to be, highly soluble in water; acids that include groups that enhance solubility in water (e.g., hydroxyl groups), examples of which include tartaric acid, citric acid, and citramalic acid, can be preferable for solubility reasons. In these and/or other embodiments, preference can be given to those organic acids which are biocompatible. Many of the organic acids listed above are used in preparing or treating food products, personal care products, and the like.

Citric acid (and its full and partial salt forms) is prevalent in the human body due to its/their role in the Krebs cycle. Because the human body tolerates citric acid (and its salts) so well, as well as the fact that it possesses multiple carboxyl groups, it constitutes a preferred organic acid. (Citrate ions also might play a tumor suppression role; see J-G Ren et al., "Citrate Suppresses Tumor Growth in Multiple Models through Inhibition of Glycolysis, the Tricarboxylic Acid Cycle and the IGF-1R Pathway," *Nature Science Reports,* 2017, 7:4537 (open source).)

The amount of any given acid employed can be determined from the target pH of a given composition and the $pK_a$ value(s) of the chosen acids in view of the type and amounts of buffer precursor compound(s) employed, discussed below.

Both to ensure that the pH of the composition is not too low and also to increase its effective solute concentration, the solute component also includes a conjugate base of at least one of the foregoing weak acids. Conjugate base(s) increase the effective amount of solutes in the composition without greatly impacting the molar concentration of hydronium ions while, simultaneously, providing a buffered pH to the composition. Ordinarily skilled artisans are able to adapt the foregoing to account for different forms of the acid and salt, as well as to swap out the salt for an increased amount of acid and a strong base (or basic solution) to achieve a substantially equivalent target pH and effective solution concentration. Like the acid(s), the amount of conjugate base(s) can be determined based on the desired composition pH and effective solute concentration.

Although not required, use of a conjugate base of the particular acid employed is typical. One preferred acid/buffer precursor combination is citric acid and an alkali metal salt of citric acid, e.g., mono-, di- or trisodium citrate.

The presence of one or more acids and one or more buffer precursors results in a solution that is buffered at or near a targeted pH value. This facilitates the ability of a composition to maintain tissue, ECM, etc., around or near cancer or pre-cancerous cells at a pH≤7, preferably ≤6.8, more preferably ≤6.6, even more preferably ≤6.4, still more preferably ≤6.2, and most preferably ≤6.0.

In some embodiments, the dissociation products of one or more separately provided conjugate bases (e.g., salts) of one or more of the acids, or the salt(s) of one or more other weak (organic) acids, are included; when present in the solute component of the composition with one or more weak acids, such salts can act as buffer precursor(s). A fraction up to a many fold excess of the salt(s) can be employed. The identity of the countercation portion of the salt is not believed to be particularly critical as long as that countercation is physiologically tolerated and preferably biodegradable, with common examples including ammonium and alkali metal ions; accordingly, where a particular conjugate base is set forth herein (e.g., sodium citrate), this is to be read as inclusive of other citrates unless a contrary indication is specifically mentioned. Where a polyacid is used, all or fewer than all of the H atoms of the carboxyl groups can be replaced with cationic atoms or groups, which can be the same or different. For example, mono-, di- and trisodium citrate all constitute potentially useful buffer precursors, whether used in conjunction with citric acid or another organic acid. However, because trisodium citrate has three available basic sites, it has a theoretical buffering capacity up to 50% greater than that of disodium citrate (which has two such sites) and up to 200% greater than that of sodium citrate (which has only one such site).

Alternatively, a buffered solution can be provided without separately adding a conjugate base by adding a strong base to solvated acid. Reference can be made to texts, articles, online calculation tools, etc., to determine how much of a given strong base, usually in aqueous form, to add to a solution containing a given amount of acid so as to provide a buffer at a given pH.

In each case, the result is a buffered solution based on dissociation products of the one or more weak acids.

(Many weak acids and conjugate bases of weak acids can be obtained in either anhydrous form or including varying amounts of water of hydration. The presence of water of hydration in such materials does not impact utility or efficacy. If a given solute sub-component is not provided in anhydrous form, the water of hydration merely must be subtracted when calculating the number of osmoles provided by that given material. For example, the term "trisodium citrate" is intended to be inclusive of both anhydrous trisodium citrate and all hydrated forms, e.g., trisodium citrate dihydrate.)

U.S. Pat. Nos. 9,314,017, 9,872,843, 10,021,876, 10,477,860, 10,780,037, 10,827,750, 11,118,143, etc., all are directed generally against biofilms and discuss efficacy increasing with increases in effective solute concentration (osmolarity) due to an abundance of solutes inducing a high osmotic pressure across a bacterium's cortical membrane, leading to lysis. That consideration is not believed to be relevant to efficacy in the present method.

Unlike compositions set forth in the aforementioned patents, the present compositions do not necessarily rely on effective solute concentration, regardless of how achieved, as a factor important to efficacy. Instead, the present compositions desire as much total citrates as possible. Given the relatively moderate pH values (see the preceding paragraph), this typically argues for using more conjugate base than acid so that, as body tissues begin to neutralize acid, the buffer that results from the acid and conjugate base acts to keep the composition's pH relatively stable. The end result of the foregoing is that the effective solute concentrations of the compositions preferably are quite high, e.g., at least 0.5, 0.75 or 1.0 Osm/L, generally at least 1.25 Osm/L, often at least 1.5 Osm/L, commonly at least 1.75 Osm/L, more commonly at least 2.0 Osm/L, typically at least 2.25 Osm/L, more typically at least 2.5 Osm/L, but the majority, if not all, of the solutes result from the acid and buffer precursor. In some embodiments, the composition has an effective solute concentration of at least ~3.0, at least ~3.25, at least ~3.5, at least ~3.75, or even at least ~4.0 Osm/L, with the upper limit being defined by the solubility limit of the solutes in the solvent component.

Unlike many of the compositions described in the patent documents listed below, the present composition does not require inclusion of surfactant in the solute component, although certain embodiments permit inclusion of one or more wetting agents which include, but are not limited to, surfactants. Types and amounts of surfactant(s) which can be included can be found in U.S. Pat. Nos. 8,940,792, 9,314,017, 9,872,843, 10,021,876, 10,477,860, 10,780,037, 10,827,750, 11,118,143, as well as U.S. Pat. Nos. 4,107,328, 6,953,772, 7,959,943, etc. (The amount of surfactant used in a given composition typically will be as low as possible, with many embodiments omitting surfactant altogether and others using a surfactant as a preservative, e.g., benzalkonium chloride at up to FDA permitted amounts.)

With respect to optional materials which can be included in the solute component of the composition, an active anti-cancer agent as well as any ingredient of one or more of the numerous treatment options mentioned in the Background section can be included as long as the mandatory solute subcomponents do not interfere with the efficacy of such ingredients.

In one aspect of the inventive method, the composition can constitute the carrying vehicle for one or more active ingredients of one of the aforementioned treatment options. For example, such an active ingredient that is soluble in water (or water plus one or more organic liquids, as described above) can be carried in a composition of the present invention in methods involving injection, elution from a solid or device, or the like.

Given the intended usages, the composition typically does not include common additives and adjuvants such as emollients, fragrances, pigments, dyes, defoamers, foaming agents, flavors, abrasives, bleaching agents, and the like. (A comprehensive listing of additives approved by the U.S. Food and Drug Administration is available as a zipped text file at www.fda.gov/media/72482/download (link active as of filing date of this application).) In certain instances, inclusion of such an additive (e.g., a dye or pigment) might be desirable to help envision the area in which a treating composition has been applied or introduced.

Utilization of one or more embodiments of the composition in the aforedescribed usages (and variants which are obvious to the ordinarily skilled artisan in view of that description) can result in reduction in the size of cancerous tumors and even precancerous lesions.

Although the utilities of composition and method have been described in connection with treating humans, no known factor or complication should prevent those utilities from being extended to mammals of all types and, perhaps, even to non-mammalian vertebrates.

As a single example of potential utility, a physician specializing in wound care was treating a diabetic patient with chronic wounds on his legs. During a visit, the doctor diagnosed a non-malignant skin cancer and recommended that it be excised. The cancerous nature of that area of the skin was confirmed by biopsy.

The patient was given BlastX™ antimicrobial wound gel (Next Science; Jacksonville, Florida) to apply to the chronic wounds in the hopes of promoting sufficient healing to permit performance of an unrelated orthopedic procedure. That product is a high osmolarity (at least 2 Osm/L calculated effective solute concentration), acidic (pH≈4, using a combination of citric acid and trisodium citrate) aqueous composition that contains 0.13% (w/v) benzalkonium chloride dispersed in a PEG vehicle.

The patient continued to be monitored for over a year, during which time the tumor shrank noticeably before disappearing altogether. Erythema was deemed to be, at worst, mild throughout numerous applications of gel.

A single-site, open label, prospective single-arm exploratory clinical study to assess the clinical and histological effects on skin healing and inflammation in wounds resulting from diagnostic skin biopsies of non-melanoma skin cancer lesions on the arms, legs or trunk was commissioned. Goals of this study were to assess clinical lesion size and appearance of diagnostic biopsy wound sites and surrounding skin lesions after 14 and 28 days of topical application of the same gel that was used on the single patient from the aforedescribed anecdotal report and to explore the histological presentation of the treated area on an excisional biopsy performed after 28 days of topical application.

The study was designed to enroll up to eight people who had undergone skin biopsy lesions. Qualifying subjects were deemed to be males and females of at least 18 years in age who were undergoing outpatient diagnostic skin biopsy of skin lesions on the extremities or trunk which were clinically suspicious for non-melanoma skin cancer.

Each subject, referred by a primary care physician or dermatologist, had a skin lesion which was clinically suspicious for non-melanoma skin cancer and deemed to be appropriate for diagnostic skin biopsy.

At the first screening visit (Visit 1), each subject's lesions were imaged and measured for surface area, surgically removed (shave or punch biopsy, at the investigator's discretion) and then imaged/measured again. The biopsy was sent for pathologic analysis and documented with a pathology report.

After the initial biopsy procedure, patients were given the aforedescribed wound gel, with instructions to apply a layer (~3 mm thickness) of it to the biopsy wound and 1 cm beyond its edge (i.e., any surrounding lesion) followed by application of a protective bandage. Application was to occur every day for 28 days.

Subjects with histological diagnoses other than non-melanoma skin cancer, upon receipt of non-qualifying biopsy result, discontinued applications of the gel and were excluded from further study participation (other than follow-up of any adverse events) and were returned to their referring physician for further treatment.

Subjects were seen for assessment and measurement of the treated wound and surrounding target skin lesion, as well as evaluation of compliance and adverse events, after 14 days (Visit 2) and 28 days (Visit 3).

At Visit 2, the lesion area was imaged/measured, and the subject was instructed to continue applying the wound gel as previously instructed.

At Visit 3, the lesion area again was imaged/measured and then the investigator performed an excisional biopsy on the entirety of any remaining lesion, using that facility's standard-of-care sterile procedure, with all excised tissue being submitted to a third-party commercial lab for standard histological evaluation. The lesion area was imaged/measured again after excision; if the excisional biopsy did not show clear margins deemed acceptable to the investigator, the subject was referred to his or her referring physician for further treatment outside of the trial. Any remaining wound gel product was collected.

A final study visit 10-14 days later (Visit 4) was scheduled for suture removal as needed, wound check (imaging and measurement) and review of biopsy results.

Tabulated below are post-diagnostic biopsy wound size areas and post-excisional biopsy wound size areas (both in $cm^2$) for the seven subjects with basal cell carcinomas on their arms who proceeded through all phases of this clinical trial. (The Visit 3 data in Table 1 were collected prior to the excisional biopsy.)

TABLE 1 wound area sizes, post-diagnostic biopsy

| | at Visit 1 | at Visit 2 | at Visit 3 |
|---|---|---|---|
| Subject A | 0.8 | 0.6 | 0.8 |
| Subject B | 1.0 | 0.7 | 0.7 |
| Subject C | 0.7 | 1.4 | 0.8 |
| Subject D | 0.5 | 1.1 | 1.0 |
| Subject E | 0.9 | 1.6 | 1.1 |
| Subject F | 0.3 | 0.2 | 0.1 |
| Subject G | 1.0 | 1.0 | 1.0 |

TABLE 2 wound area sizes, post-excisional biopsy

| | at Visit 3 | at Visit 4 |
|---|---|---|
| Subject A | 16 | 15 |
| Subject B | 2.2 | 0.7 |
| Subject C | 23.0 | (a) |
| Subject D | 6.2 | (a) |
| Subject E | 2.6 | 2.4 |
| Subject F | 3.1 | 2.4 |
| Subject G | 8.0 | 5.7 |

(a) Data not received from investigator

Analysis of the post-excisional biopsy samples showed no signs of cancer in those collected from Subjects A, C and F. In other words, cancerous cells had been eliminated in 3 out of 7 subjects (43%) after only 28 days of treatment with a non-optimized topical product.

As evident from the foregoing, general preferences regarding features, ranges, numerical limitations and embodiments are, to the extent feasible and as long as not interfering or incompatible, envisioned as being capable of being combined with other such generally preferred features, ranges, numerical limitations and embodiments.

The following embodiments are specifically contemplated. Any embodiment relating to a method of use involving a composition is intended to be read as also relating to the composition for use in that method, and any use of "comprising" also contemplates less open transition terms including "consisting essentially of" and "consisting of."

Treatment Embodiments

T1: A method for selectively or preferentially reducing the amount of Fe ions available to cancer cells or pre-cancerous cells, comprising introducing to an area of a body which contains such cells an effective amount of an aqueous, acidic, pH buffered composition that comprises dissociation products of a soluble weak acid and a salt of a weak acid, wherein the composition has a pH≤6.5.

T2: The method of T1 wherein said composition has a pH from 3.0 to 6.5.

T3: The method of T2 wherein said composition has a pH from 3.2 to 6.0.

T4: The method of T3 wherein said composition has a pH from 3.4 to 5.5.

T5: The method of any of T1-T4 wherein said soluble weak acid is an organic acid.

T6: The method of T5 wherein said organic acid is one or more of tartaric acid, citric acid, and citramalic acid.

T7: The method of T6 wherein said organic acid comprises or is citric acid.

T8: The method of any of T1-T7 wherein said salt of a weak acid comprises a salt of an organic acid.

T9: The method of T8 wherein said organic acid is one or more of tartaric acid, citric acid, and citramalic acid.

T10: The method of T9 wherein said organic acid comprises or is citric acid.

T11: The method of any of T1-T10 wherein said composition has an effective solute concentration of at least 0.5 Osm/L.

T12: The method of T11 wherein said composition has an effective solute concentration of at least 0.75 Osm/L.

Use Embodiments

U1: Use of an aqueous, acidic, pH buffered composition that comprises dissociation products of a soluble weak acid and a salt of a weak acid, wherein the composition has a pH of 6.5 or less, for selectively or preferentially reducing the amount of Fe ions available to cancer cells or pre-cancerous cells.

U2: The use of U1 wherein said composition has a pH from 3.0 to 6.5.

U3: The use of U2 wherein said composition has a pH from 3.2 to 6.0.

U4: The use of U3 wherein said composition has a pH from 3.4 to 5.5.

U5: The use of any of U1-U4 wherein said soluble weak acid comprises an organic acid.

U6: The use of U5 wherein said organic acid is one or more of tartaric acid, citric acid, and citramalic acid.

U7: The use of U6 wherein said organic acid comprises or is citric acid.

U8: The use of any of U1-U7 wherein said salt of a weak acid comprises a salt of an organic acid.

U9: The use of U8 wherein said organic acid is one or more of tartaric acid, citric acid, and citramalic acid.

U10: The use of U9 wherein said salt of a weak acid comprises a salt of citric acid.

U11: The use of any of U1-U10 wherein said composition has an effective solute concentration of at least 0.5 Osm/L.

U12: The use of U11 wherein said composition has an effective solute concentration of at least 0.75 Osm/L.

Also contemplated are any of the foregoing treatment and use embodiments where the composition reduces the pH of cells, extracellular matrix, and/or fluids below a point where arriving $Fe^{+3}$ ions are prevented, or at least greatly inhibited, from entering cancer cells or pre-cancerous cells. Specifically contemplated are those embodiments where the prevention or inhibition of arriving $Fe^{+3}$ ions from entering the cancer cells or pre-cancerous cells results in the weakening and/or death of the cancer cells or pre-cancerous cells.

That which is claimed is:

1. A treatment method involving selectively or preferentially reducing the amount of Fe ions available to cancer cells or pre-cancerous cells, said method comprising introducing to an area of a body which contains such cells an effective amount of a buffered composition that consists of (a) a solvent component that comprises water and (b) a solute component that comprises anions of a soluble weak acid, hydronium ions, and cations of a strong base, said composition having a pH of 6.5 or less.

2. The method of claim 1 wherein said soluble weak acid is citric acid.

3. The method of claim 2 wherein said cations of a strong base are alkali metal ions.

4. The method of claim 1 wherein said composition has an effective solute concentration of at least 0.5 Osm/L.

5. The method of claim 4 wherein said composition has an effective solute concentration of at least 0.75 Osm/L.

6. The method of claim 4 wherein said composition has a pH from 3.0 to 6.5.

7. The method of claim 6 wherein said composition has a pH from 3.2 to 6.0.

8. The method of claim 7 wherein said composition has a pH from 3.4 to 5.5.

9. The method of claim 1 wherein said composition has a pH from 3.0 to 6.5.

10. The method of claim 9 wherein said composition has a pH from 3.2 to 6.0.

11. The method of claim 10 wherein said composition has a pH from 3.4 to 5.5.

12. The method of claim 1 wherein said solvent component consists of water.

13. The method of claim 12 wherein said composition is carried in a vehicle that results in a semi-solid, said composition eluting therefrom to said body area.

14. The method of claim 1 wherein said solvent component consists of water and no more than 25% (w/v) of one or more organic liquids.

15. The method of claim 14 wherein said composition is carried in a vehicle that results in a semi-solid, said composition eluting therefrom to said body area.

16. The method of claim 14 wherein said solute component further comprises an active anti-cancer agent.

17. The method of claim 16 wherein said composition is carried in a vehicle that results in a semi-solid, said composition eluting therefrom to said body area.

18. The method of claim 1 wherein each of the following is true:

said soluble weak acid is citric acid, said cations of a strong base are alkali metal ions, said composition has an effective solute concentration of at least 0.75 Osm/L, and said composition has a pH from 3.4 to 5.5.

19. The method of claim 18 wherein said composition is carried in a vehicle that results in a semi-solid, said composition eluting therefrom to said body area.

20. The method of claim 18 wherein said solute component is free of surfactants.

* * * * *